(12) United States Patent
Rasmussen et al.

(10) Patent No.: US 9,278,017 B2
(45) Date of Patent: Mar. 8, 2016

(54) IMPLANT RELEASE MECHANISM

(75) Inventors: Erik E. Rasmussen, Slagelse (DK); Bent Øhlenschlaeger, Lille Skensved (DK)

(73) Assignee: Cook Medical Technologies LLC, Bloomington, IN (US)

( * ) Notice: Subject to any disclaimer, the term of this patent is extended or adjusted under 35 U.S.C. 154(b) by 416 days.

(21) Appl. No.: 11/998,530

(22) Filed: Nov. 30, 2007

(65) Prior Publication Data
US 2008/0140178 A1    Jun. 12, 2008

Related U.S. Application Data

(60) Provisional application No. 60/861,861, filed on Nov. 30, 2006.

(51) Int. Cl.
| | |
|---|---|
| *A61F 2/95* | (2013.01) |
| *A61F 2/01* | (2006.01) |
| *A61F 2/07* | (2013.01) |
| *A61F 2/966* | (2013.01) |
| *A61B 17/12* | (2006.01) |

(52) U.S. Cl.
CPC .......... *A61F 2/95* (2013.01); *A61B 2017/12054* (2013.01); *A61F 2/01* (2013.01); *A61F 2/07* (2013.01); *A61F 2002/9505* (2013.01); *A61F 2002/9511* (2013.01); *A61F 2002/9665* (2013.01)

(58) Field of Classification Search
CPC ........... A61F 2/95; A61F 2/962; A61F 2/966; A61F 2002/9511; A61F 2002/9534
USPC .................................................. 623/1.11, 1.23
See application file for complete search history.

(56) References Cited

U.S. PATENT DOCUMENTS

| | | | | |
|---|---|---|---|---|
| 4,913,141 | A | * | 4/1990 | Hillstead ....................... 623/1.11 |
| 5,019,085 | A | | 5/1991 | Hillstead |
| 5,779,732 | A | * | 7/1998 | Amundson ................... 623/1.15 |

(Continued)

FOREIGN PATENT DOCUMENTS

| | |
|---|---|
| EP ISR/PCT/US07/024714 | 5/2008 |
| EP WO/PCT/US07/024714 | 5/2008 |

(Continued)

OTHER PUBLICATIONS

Translation of Japanese Office Action for corresponding JP 2009-539361 dated May 8, 2012 5 pages.

(Continued)

*Primary Examiner* — Sarah W Aleman
(74) *Attorney, Agent, or Firm* — Brinks Gilson & Lione

(57) ABSTRACT

An implant release mechanism for releasing, for example, a stent (60) is provided with three restraining wires (62) which pass in the space between a wire guide catheter (24) and a pusher sheath or dilator (30) and are arranged substantially equi-angularly threrearound. Each restraining wire (62) holds both the proximal and distal ends of the stent (60), in this case each holding a proportion of the ends of the stent (60). When the restraining wires (62) are pulled they will first unwrap from the proximal end of the stent (60) and will then release the distal end of the stent (60) so as to allow the stent to become fully deployed within the lumen of the patient. The use of common release wires improves deployment of implants and reduces the number and volume of components in the device, thereby allowing it to occupy a smaller volume.

14 Claims, 4 Drawing Sheets

(56) References Cited

U.S. PATENT DOCUMENTS

| | | |
|---|---|---|
| 6,183,481 B1 | 2/2001 | Lee et al. |
| 6,346,118 B1* | 2/2002 | Baker et al. ............... 623/1.12 |
| 6,551,350 B1* | 4/2003 | Thornton et al. ........... 623/1.13 |
| 7,637,932 B2* | 12/2009 | Bolduc et al. ............... 623/1.11 |
| 2003/0199918 A1 | 10/2003 | Patel et al. |
| 2004/0073289 A1* | 4/2004 | Hartley ....................... 623/1.13 |
| 2005/0090834 A1* | 4/2005 | Chiang et al. .............. 623/1.11 |
| 2005/0119722 A1* | 6/2005 | Styrc et al. ................. 623/1.12 |
| 2006/0142836 A1* | 6/2006 | Hartley et al. ............. 623/1.11 |

FOREIGN PATENT DOCUMENTS

| | | |
|---|---|---|
| JP | 2002-503114 A | 1/2002 |
| JP | 2008-514370 A | 5/2008 |
| WO | WO9853761 * | 12/1998 ............... A61F 2/06 |
| WO | WO 03/101346 A1 | 12/2003 |
| WO | WO2006/037086 A1 | 4/2006 |

OTHER PUBLICATIONS

Examiner's First Report for corresponding AU patent application No. 2007325652 dated Feb. 20, 2012, 2 pages.
First Examination Report for corresponding EP patent application No. 07862422.8 dated Oct. 29, 2012, 7 pages.
Second Examination Report for corresponding EP patent application No. 07862422.8 dated Jun. 10, 2013, 8 pages.
International Preliminary Report on Patentability for corresponding PCT/US2007/024714 dated Feb. 18, 2009, 13 pages.

* cited by examiner

IMPLANT RELEASE MECHANISM

CROSS-REFERENCE TO RELATED APPLICATIONS

This application claims priority of provisional application Ser. No. 60/861,861, filed Nov. 30, 2006.

TECHNICAL FIELD

The present invention relates to a release mechanism for releasing an implant from a deployment device, for example for releasing a stent or stent-graft. The present invention is particularly suited for releasing a dissection stent from a deployment device.

BACKGROUND OF THE INVENTION

When an expandable endovascular prosthesis or implant, such as a stent, is deployed, it is very important to position it at the precise desired location within the patient's lumen. With some prior art stent delivery systems, as soon as the covering sheath is withdrawn to expose the underlying stent, the distal end of the stent expands in a rapid and irregular way, with the risk that one or more of the struts of the stent is deformed irregularly, such as being bent backwards. The risk of such an occurrence is increased in cases where the distal end of the delivery device on which the stent is located is not in the middle of the vessel.

Moreover, in the final stages of deployment, when the sheath slides over and beyond the distal end of the stent, this will expand in a manner which is difficult to control. This lack of control makes the placement of the implant less accurate and can also lead to damage to the intima of the vessel.

These problems tend to be exacerbated in the deployment of dissection stents for treating aortic dissections. The reason is that dissection stents tend to be very pliable and therefore require careful deployment in order not to be twisted, damaged or otherwise compromised.

In order to mitigate the problems described above, it is known to restrain the ends of the implant so as to keep it in a substantially compressed form on withdrawal of the sheath. The ends are then released to complete the deployment of the device. For example, in the case of a stent or stent-graft, the ends thereof are held tightly against the deployment catheter until released by the clinician. For this purpose, there are provided release devices at both the distal and the proximal ends of the stent or stent-graft. It is known to use release wires for the release devices, which release wires tie the ends of the stent or stent-graft until release is effected.

For example, US-2006/0,142,836 discloses a delivery device in which the proximal end of the stent graft is held by a plurality of restraining wires coupled through sutures to the apices of the proximal-most hoop of the stent. If desired, the distal end of the stent could be likewise secured by a plurality of distal end restraining wires. In order to release the stent-graft, the sheath is removed, then the proximal and distal ends released, as determined by the surgeon after final alignment of the stent-graft in the patient's lumen, by manipulation of a release mechanism which loosens the restraining wires.

US-2004/0,073,289 discloses a delivery system which is provided with a series of restraining wires for holding the proximal end of the stent-graft and a distal collar for restraining the distal end of the stent-graft. The two release mechanisms are deployable separately to release the proximal and distal ends of the stent-graft as required by the particular medical procedure.

These prior art systems can mitigate the problems described above. However, they can be difficult for a surgeon to deploy by requiring the provision of different release mechanisms at the proximal or external manipulation end of the deployment device.

In the case of certain types of implant, such as dissection stents, the deployment of the stent involves particular difficulties in light of the delicate nature of the stent, that is because of its extreme flexibility. It has been known for such a stent to become twisted as a result of rotation of the delivery device during the deployment operation, caused by having to deploy different release mechanisms and at different times.

Another problem with these prior art systems is that they necessarily take up a certain volume within the delivery device, which limits the minimum achievable diameter of the delivery device.

SUMMARY OF THE INVENTION

The present invention seeks to provide an improved implant release mechanism.

According to an aspect of the present invention, there is provided an implant release mechanism including an elongate implant support provided with proximal and distal implant restraining locations; proximal and distal wire holding elements; and at least one restraining wire, wherein said at least one restraining wire is restrained by said proximal and distal wire holding elements, so as to restrain an implant at both said proximal and distal locations.

The provision of at least one restraining wire which can restrain both ends of an implant can reduce the number of restraining devices required to hold the implant in its compressed state prior to its deployment, thereby reducing the volume of the components of the delivery device and therefore enabling a reduction in its outer diameter. This allows for the provision of smaller delivery devices which can be used to deliver implants in smaller lumens.

Furthermore, the or each common release wire can be manipulated by a single release mechanism, simplifying the proximal end of the deployment device which the surgeon has to manipulate and simplifying the movements required to be performed by the surgeon.

In addition to the advantages described above, the provision of a common release wire can provide, at the option of the surgeon, release of both ends of the implant in a continuous and smooth operation, with the proximal end of the implant being released first and then the distal end, as viewed from the heart. This can substantially facilitate the correct placement of the entire of the implant and significantly reduce the chances of errors such as twisting of the implant during the deployment process.

In the preferred embodiment, the implant release mechanism is provided with a plurality of restraining wires, each of which is arranged to hold at least a portion of both the proximal and the distal ends of an implant.

Advantageously, there are provided three restraining wires. It has been found that this number provides good restraining properties and yet does not unnecessarily add bulk to the deployment device, thereby allowing the device to be of reduced outer diameter compared to prior art systems.

Preferably, the or each restraining wire is formed from nitinol.

In the preferred embodiment, the proximal and distal implant restraining locations include wire holding elements. Typically, these include closed channels or bores through which the restraining wire or wires can pass. Advantageously, the or each distal restraining location, at the tip of the deployment device, includes a bore receiving in a tight-fit manner or otherwise in a releasably secured manner, ends of the wire or wires to hold these until they are withdrawn by the release action.

According to another aspect of the present invention, there is provided an assembly including a deployment device and an implant, wherein the deployment device includes an implant release mechanism including an elongate implant support provided with proximal and distal implant restraining locations; proximal and distal wire holding elements; and at least one restraining wire, which restraining wire is restrained by said proximal and distal wire holding elements, so as to restrain the implant at both said proximal and distal locations.

In an embodiment, the implant is a stent or stent-graft. In another embodiment, the implant is a filter or occlusion device.

Advantageously, the implant is provided with one or more threads through which the restraining wires pass. The threads may be made of suture material. Preferably, the threads are coupled to apices of stents at the extremities of the implant. In one embodiment, a single thread is coupled to all of the apices. In another embodiment, each apex is provided with a loop of thread.

BRIEF DESCRIPTION OF THE DRAWINGS

Embodiments of the present invention are described below, by way of example only, with reference to the accompanying drawings, in which.

DETAILED DESCRIPTION

Figure 1:
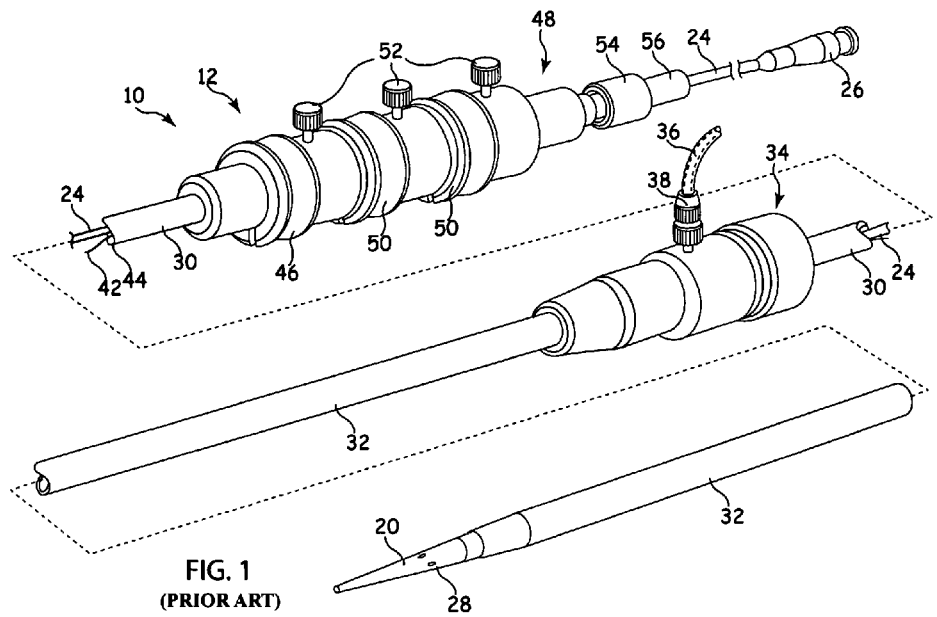
FIGS. 1 and 2 show an example of a known deployment device.
Figure 2:
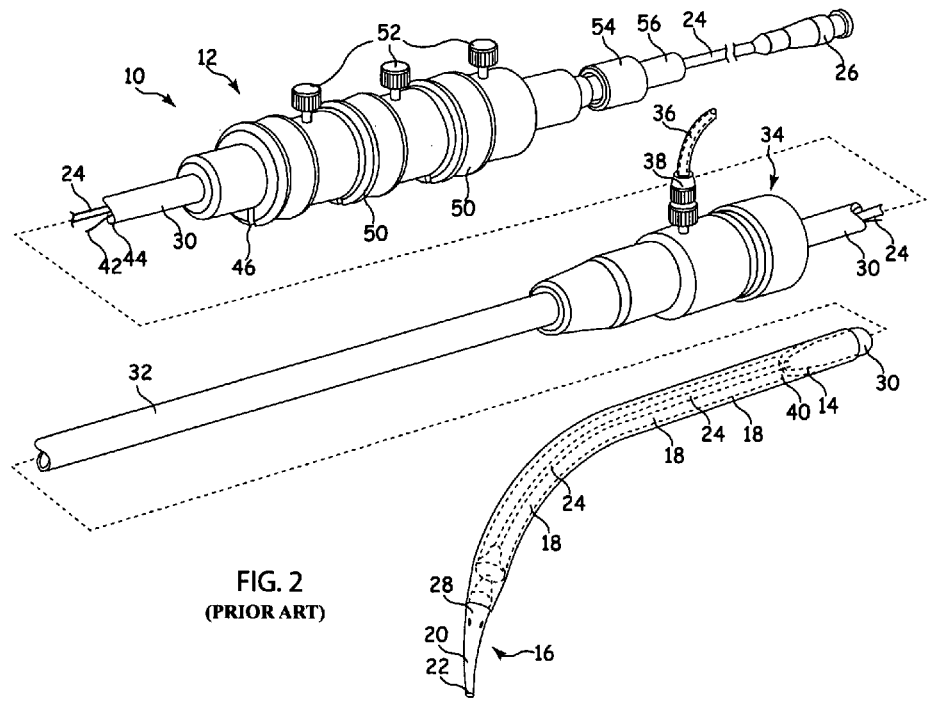

Referring to FIGS. 1 and 2, there is shown an example of known delivery device, which is useful in understanding the principles of the release mechanism taught herein. The delivery device 10, hereinafter referred to as the introducer, includes an external manipulation section 12 which is operated by a surgeon or clinician and a distal end which is introduced intraluminally into a patient. The distal end includes a distal attachment region 14 and a proximal attachment region 16. The distal attachment region 14 and the proximal attachment region 16 secure the distal and proximal ends of the implant 18, respectively.

During the medical procedure to deploy the implant 18, the distal end of the device 10 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a flexible dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during the placement and deployment phases of the medical procedure.

A guide wire catheter 24, conventionally made from a flexible thin walled metal tube, is fastened to the flexible tip 20. The guide wire catheter 24 is flexible so that the introducer 10 can be advanced along a relatively tortuous vessel, starting from, for example, the femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible tip 20. Therefore, reagents introduced into connection device 26 will flow to and emanate from the apertures 28.

A pusher sheath or rod 30 (hereinafter referred to as a pusher member), typically made from a plastics material, is mounted coaxially over and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft, vena cava filter, occlusion device or any other implant or prosthesis deliverable by such a device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the flexible tip 20 of the proximal attachment region 16 while the implant 18 is held in a compressed state by an external force. A suitable distal attachment (retention) section (not visible in this view) is coupled to the pusher rod 30 and retains a distal end 40 of the implant 18 during the procedure. The distal end of the implant 18 is provided with a loop (not shown) through which a distal trigger wire 42 extends. The distal trigger wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least two trigger wire actuation sections 46, 50 mounted on a body 48, in turn mounted onto the pusher member 30. In this example there are provided three wire release mechanisms. The guidewire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18.

A haemostatic seal (not shown) is included so that the release wires can extend out through the body 48 without unnecessary blood loss during the medical procedure.

A proximal portion of the external manipulation section 12 includes a pin vice 54 mounted onto the proximal end of the body 48. The pin vice 54 has a screw cap 56. When screwed in, vice jaws (not shown) of the pin vice 54 clamp against or engage the guidewire catheter 24. When the vice jaws are engaged, the guidewire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for positioning. The proximal end of the self-expanding stent, however, is still retained at the flexible tip 16 by means of the release wires. Also, the distal end of the stent or stent-graft 18 will still retained within the sheath 32.

Next, the pin vice 54 is released to allow small movements of the guidewire catheter 24 with respect to the pusher rod 30 to allow the stent or stent-graft 18 to be lengthened, shortened, rotated or compressed for placement within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vice 54, the screw cap 56 and the connection unit 26.

Next, the screw cap 56 of the pin vice 54 is loosened, after which the inner catheter 24 can be pushed in a proximal direction to move the flexible tip 20 in a proximal direction. When the flexible tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

The example prior art device shown in FIGS. 1 and 2, as would be readily apparent to the person skilled in the art, includes separate release wire mechanisms for releasing the proximal and distal ends of the implant 18, as well as specific locks and release mechanisms 50, 52 for operating the release wires.

Figure 3:
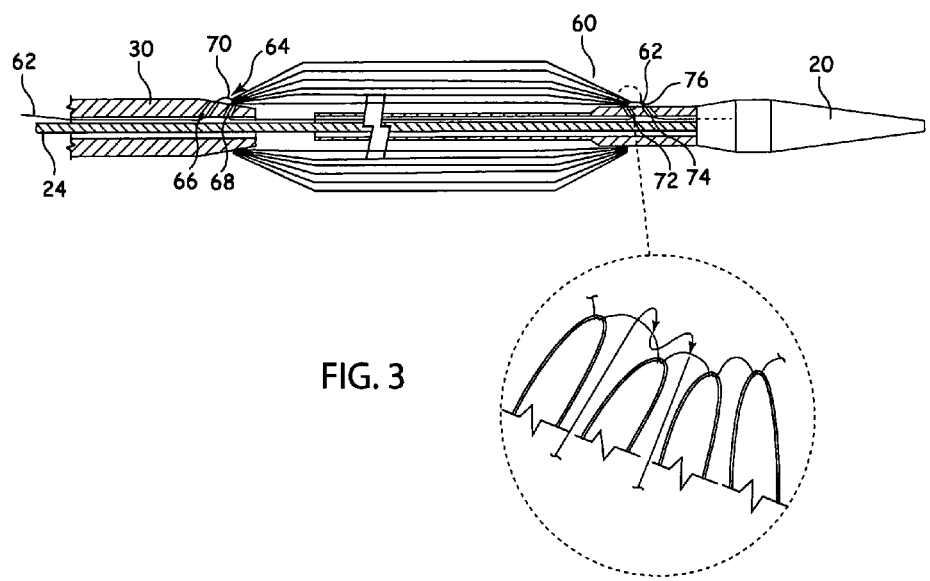
FIG. 3 shows in schematic form an embodiment of implant release mechanism coupled to a dissection stent.

Referring now to FIG. 3, there is shown an embodiment of implant release mechanism, in this case being part of a delivery device analogous to that of FIGS. 1 and 2 but incorporating an example of the release mechanism taught herein.

The embodiment of FIG. 3 is shown holding a stent 60, in this example a dissection stent, although it is to be understood that the principles taught herein can be used to hold and restrain any implant, including other forms of stent, stent-grafts, vena cava filters, occlusion devices and any other implants and prostheses which can be delivered by such delivery devices.

The example in FIG. 3 shows a single restraining wire 62 which passes in the space between the wire guide catheter 24 and the pusher sheath or dilator 30. At an end of the dilator 30 which provides the distal fixation point 64, there are provided two bores 66, 68 which, in this example, are at an angle of around 90° to one another so as to enable the restraining wire 62 to pass through both bores to provide a loop 70 as shown in FIG. 3 in particular.

At the proximal end of the implant attachment region and in particular within the wall of the flexible tip 20 adjacent the proximal end of the implant 60, there are provided bores 72, 74 equivalent to the bores 66, 68 in the distal attachment region, these being adjacent a proximal fixation position 62. The restraining wire 62 also forms a loop 76 as it passes through the two bores 72, 74.

The end of the restraining wire 62 is fixed, for example by an interference fit or by suitable adhesive, to a location on the inside of the flexible tip 20 but in such a manner that the wire 62 can be withdrawn from its fixation location upon application of a pulling force by the surgeon through an appropriate control element or handle at the external manipulation section 12 of the delivery device 10. The manner in which the end of the restraining wire 62 is held within the flexible tip 20 is conventional in the art so need not be described in further detail herein.

FIG. 3 shows a single restraining wire 62. However, in the preferred embodiment, a plurality of restraining wires 62 is provided, most preferably three, arranged substantially equi-angularly around the pusher sheath 30 and dilator 20. It is considered that using three restraining wires 62 provides the optimum solution in terms of restraining the implant in a substantially compressed condition on the delivery device until it has to be deployed, whilst not providing too many components within this tip section of the delivery device, thereby enabling the delivery device to have a small outer diameter.

In the view of FIG. 3, the sheath 32 which would normally cover the implant 60 and part of the flexible tip 20 adjacent the implant 60 has been removed, such that the implant 60 is no longer kept in its compressed state by the force applied to it normally by the sheath 32. As can be seen in FIG. 3, in this condition, the central portion of the stent 60 has expanded to the extent possible whilst its proximal and distal ends remain constrained at the fixation points 62 and 64.

The ends of the stent 60 will only be released to expand once the restraining wires 62 have been removed, typically by applying a pulling force to the wires 62 from the external manipulation section 10, in a manner known in the art. In this particular case, since there is a common restraining wire 62 holding both the proximal and distal ends of the stent 60 (particularly three restraining wires 62 each holding a proportion of the ends of the stent 60) when the restraining wire or wires 62 are pulled they will first unwrap themselves from the proximal end of the stent 60. This will typically happen as the ends of the release wires 62 pass through their respective bores 74 then into the bores 72. Thus, the proximal end of the stent 60 is released to expand first.

Upon further pulling of the same restraining wire or wires 62, preferably using the same release mechanism, the end of the restraining wire will eventually feed through the bores 68 and then the bores 66, thereby to release the distal end of the stent 60 so as to become fully deployed within the lumen of the patient.

Figure 4:
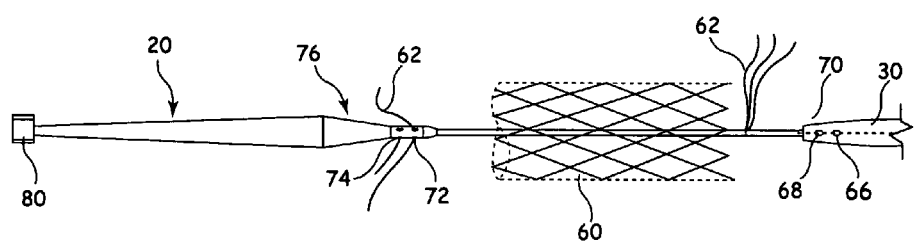
FIG. 4 is a side elevational view of the device of FIG. 3 in the course of assembly.

Referring now to FIG. 4, there is shown the embodiment of implant release mechanism of FIG. 3; in the course of the assembly of a stent 60 onto the delivery device 10. FIG. 4 is shown in schematic form simply to illustrate the provision of three restraining wires 62, as the method of fixing the ends of the stent 60 is described in further detail in connection with FIGS. 5 to 8. In FIG. 4, the stent 60 is shown in a fully expanded form, before its ends are constrained to the proximal and distal fixation points 70, 76 of the delivery device. The restraining wires 62 are also shown in loose form, prior to fitting, as described above and also below.

A holding cap 80 is provided, if desired, to hold the end of the flexible tip 20 during the assembly process.

Figure 5:
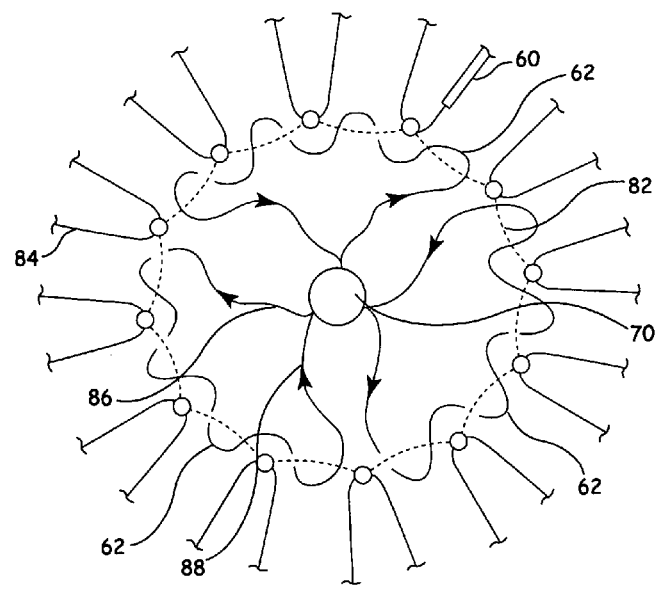
FIG. 5 shows in schematic form an embodiment of threading scheme for coupling the ends of the stent to the restraining wires.

Referring now to FIG. 5, there is shown an embodiment of threading scheme for coupling the restraining wires 62 to the distal end of the stent 60. In this embodiment, there is provided a common thread 82, which may be a conventional suture thread, tied at each apex 84 of the endmost stent ring of the stent 60. For this purpose, the suture thread 82 is knotted at each apex 84 and is preferably of such a length that it allows this end of the stent 60 to expand as much as the other sections of the stent 60 or by any amount considered appropriate for the particular medical application in question.

Each restraining wire 62 is looped around the portion of suture thread 82 between each apex 84, with the two ends 86, 88 being fed into the appropriate bores 66, 68, respectively. Thus, when the restraining wires 62 are pulled into their restraining position, as shown in FIG. 3 and in particular in FIG. 6, the restraining wires 62 pull the suture thread 82 into the loop 70 formed by the restraining wire 62 between the two bores 66, 68, thereby pulling the distal end of the stent 60 into the compressed form shown in FIG. 6.

Figure 6:
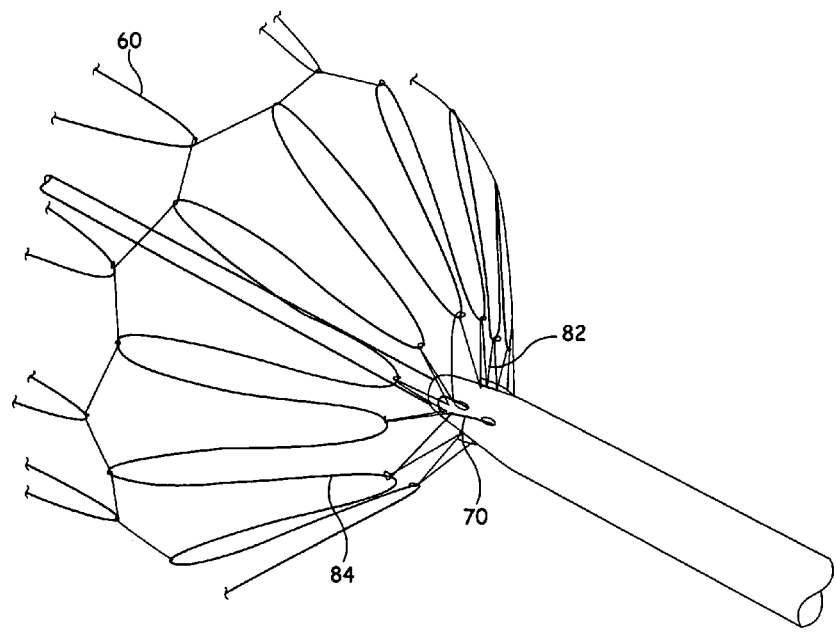
FIG. 6 shows the distal end of the stent restrained to the dilator of the device of FIG. 3.
Figure 7:
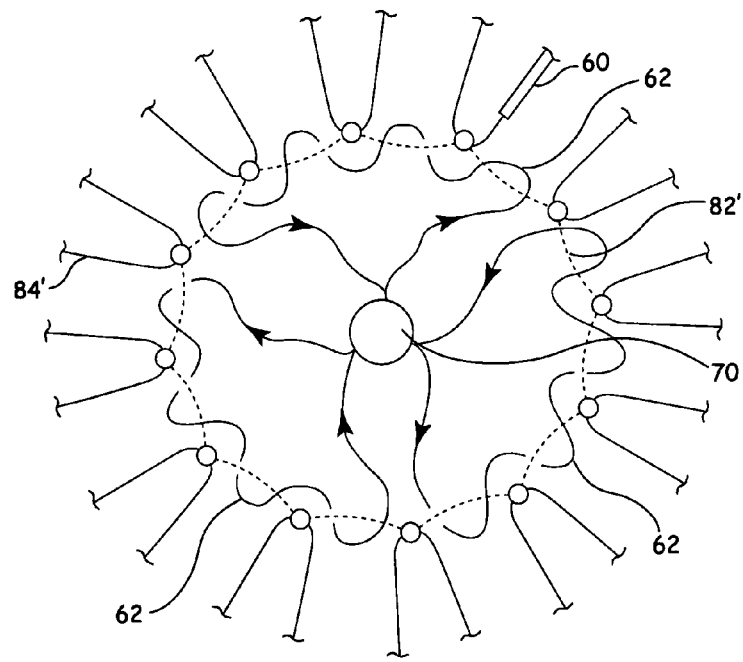
FIG. 7 shows an embodiment of threading scheme for coupling the restraining wires to the proximal end of the stent.
Figure 8:
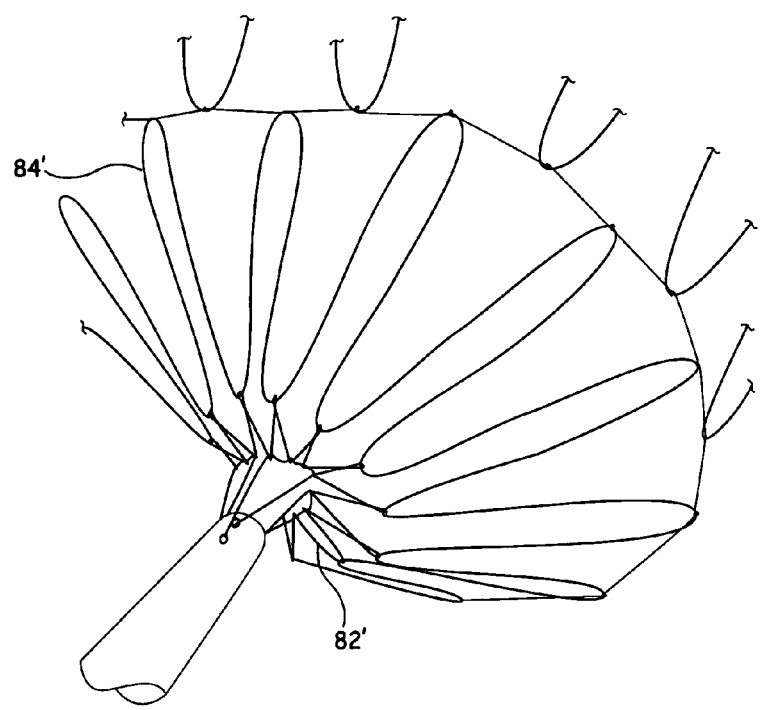
FIG. 8 shows the proximal end of the stent restrained onto the flexible tip stent section of the device of FIG. 3.

The proximal end of the stent 60 is also restrained by the restraining wires 62, in a manner similar to that shown in FIGS. 5 and 6. This is shown in FIGS. 7 and 8, in which common reference numerals have been used and in which in the apices of the proximal-most stent ring identified by reference numeral 84' and the suture thread is identified by reference numeral 82'.

A common restraining wire 62 will restrain, in the example shown in FIGS. 3 to 8, a proportion of the distal end of stent 60 as well a proportion of the proximal end of the stent 60. In the example of FIGS. 3 to 8, each restraining wire 62 will restrain a third of the distal end of the stent 60 as well as a third of the proximal end of a stent 60.

Upon withdrawing of the restraining wire 62, therefore, this will be released from its holding position within the flexible tip 20 and will first unravel from the proximal end of the stent 60. Eventually, as it is withdrawn further, each restraining wire 62 will unravel from the distal end of the stent 60. In the preferred embodiment, the three restraining wires 62 are actuated by the same actuating mechanism, for example a handle, possibly of the type shown in FIGS. 1 and 2, such that the entirety of the proximal end of the stent 60 will be released at the same time. Subsequently, the entirety of the distal end will be released.

In some applications it may be desired to release the proximal and/or distal ends of the stent 60 in sections, in which case the individual restraining wires 62 could be withdrawn separately from one another.

Thus, in contrast to the prior art example of FIGS. 1 and 2, it is only necessary to have a single wire actuation section 50 to actuate the restraining wires 62 to release the stent 60. This has the advantage of providing only a single actuation device for a surgeon to operate, thereby simplifying the surgeon's task. Furthermore, since a single release mechanism can be used, the release of the entirety of the stent 60 can be effected by the same procedure, (for example the same withdrawing or pulling action by the surgeon) which therefore enables this deployment phase of the stent 60 to be carried out smoothly and more accurately than with prior art devices.

The restraining wires 62 can be made of any suitable material, including Nitinol any other flexible metal or alloy, a polymeric fibre or any other suitable material.

The embodiment of FIGS. 3 to 8 includes three restraining wires 62. However, the teachings herein are not limited to this number. It is envisaged that in some applications a single release wire 62 can be provided to restrain the entirety of each end of the stent 60 or other device to be implanted. Similarly, there may be provided two restraining wires or more than three. Provision of three is, however, preferred in that it optimises the tensile force required to withdraw the restraining wires 62 in conjunction with the overall volume required for the assembly.

The embodiment of FIGS. 3 to 8 also uses a suture thread 82, 82' around which the restraining wires are looped. However, this particular arrangement of suture thread 82, 82' is not essential. It is envisaged, for example, that in some applications the restraining wire 62 can be looped around the apices of the stent sections, without any need for a holding thread of the type shown in FIGS. 3 to 8. In another embodiment, each apex 84 could be provided with its own individual loop of suture thread, through which a restraining wire 62 can be made to pass. In yet another embodiment, some of the apices 84 could be provided with a long loop of suture thread which is then passed through adjacent apices 84 which are not provided with such suture thread and through which the restraining wire 62 can be made to pass, in a manner similar to that described in US-2006/0142836.

Although the embodiments disclosed above have been described in connection with a stent, this restraining mechanism can be used to restrain any implant which can be carried by such a delivery device. It can be used, for example, to hold any other type of stent, a stent-graft, a filter such as that disclosed, for example, in US-2003/0199918, an occlusion device or any other implant or prosthesis deliverable by such a delivery device.

Although specific embodiments have been described above they are not to be considered limiting to the invention. The scope of the teachings herein is as set out in the appended claims.

What is claimed is:

1. An implant deployment system, comprising:
   a deployment device; and
   a self-expanding implant disposed on the deployment device and having a proximal end, a distal end, a central portion between the proximal end and the distal end, a first expanded configuration and a second expanded configuration, a stent disposed adjacent one of or both of the proximal and distal ends and having apices;
   the deployment device comprising:
   an implant release mechanism for releasably retaining the implant on the deployment device, the implant release mechanism including an elongate implant support having a proximal implant restraining location disposed substantially adjacent the implant proximal end and a distal implant restraining location disposed substantially adjacent the implant distal end; a proximal wire holding element at the proximal implant restraining location and a distal wire holding element at the distal implant restraining location; and at least one common release wire having an implant proximal end restraining portion and an implant distal end restraining portion, wherein one of or both of the proximal wire holding element and the distal wire holding element comprises a single thread having at least three loops, wherein each of the at least three loops of the one or both of the proximal wire and distal wire holding elements engages one or more of the apices and an implant end restraining portion of the at least one common release wire, and wherein each loop of the plurality of loops forms a loop between an apex of the apices and the at least one common release wire, and wherein each of the apices is coupled to one of the plurality of loops;

where in the first expanded configuration the release wire proximal end restraining portion is restrained by the proximal wire holding element and the release wire distal end restraining portion is restrained by the distal wire holding element so as to restrain the implant at both the proximal and distal locations; and where in the first expanded configuration the at least one release wire restrains both the proximal and distal ends of the implant without restraining the central portion of the implant such that the central portion is at least partially expanded relative to the proximal and distal implant ends.

2. The implant deployment system of claim 1, further including a plurality of release wires, each of which being arranged to hold at least a portion of both the proximal and the distal ends of an implant.

3. The implant deployment system of claim 2, further, including three release wires.

4. The implant deployment system of claim 2, wherein the or each release wire is formed from Nitinol.

5. The implant deployment system of claim 1, wherein the wire holding elements include closed channels or bores through which the release wire or wires can pass.

6. The implant deployment system of claim 1, wherein the distal holding element includes a bore receiving in a tight-fit manner or otherwise in a releasably secured manner, ends of the release wire or wires.

7. The implant deployment system of claim 1, wherein the implant is a vena cava filter or occlusion device.

8. The implant deployment system of claim 1, wherein the single thread is made of suture material.

9. The implant deployment system of claim 1, wherein both of the proximal wire holding element and the distal wire holding element comprises at least three loops.

10. An implant deployment system comprising deployment device and an implant disposed on the deployment device, wherein the deployment device includes an implant release mechanism for releasably retaining the implant, the implant including restrained proximal and distal ends, an unrestrained central portion between said proximal and distal ends, a first expanded configuration and a second expanded configuration, where in the first expanded configuration the central portion of the implant is unrestrained and expanded relative to the proximal and distal ends and the proximal and distal ends are restrained; the implant release mechanism including an elongate implant support provided with proximal and distal implant restraining locations; proximal and distal wire holding elements; and at least one common release wire, wherein said at least one common release wire is restrained by said proximal and distal wire holding elements, so as to restrain the implant at both the proximal and distal locations, the at least one common release wire arranged so as to restrain the proximal and distal ends of the implant without restraining the central portion of the implant, and wherein the wire holding elements include closed channels or bores through which the release wire or wires can pass; and wherein the distal holding element includes a bore receiving in a tight-fit manner or otherwise in a releasably secured manner, ends of the release wire or wires;

wherein at least one of the proximal wire holding element and the distal wire holding element comprises at least three loops of a single thread, wherein the at least three loops engage apices at an end of the implant and the at least one common release wire, and wherein each loop forms a loop between at least one apex and the at least one common release wire, and each apex is coupled to one of the at least three loops.

11. The implant deployment system of claim 10, wherein both of the proximal wire holding element and the distal wire holding element comprise at least three loops.

12. A deployment system for an implant, comprising:
a deployment device having implant retaining section having proximal and distal ends, an implant having a proximal end, a distal end, and a central section and disposed on the device at the implant retaining section, proximal and distal retaining mechanisms approximately coincident with the respective implant proximal and distal ends, at least one common release wire releasably attached to both the proximal and distal retaining mechanisms and to the proximal and distal ends of the implant, the at least one common release wire restraining the proximal and distal ends of the implant without constraining the central section, and a single release wire release mechanism, wherein the implant has a first expanded configuration where the proximal and distal ends of the implant are restrained and the central section is expanded relative to the proximal and distal ends of the implant, wherein one or both of the proximal and distal retaining mechanisms comprises at least three loops of a single thread, each loop engaging an end of the implant and engaging the at least one common release wire, and wherein each loop forms a loop between an end of the implant and the at least one common release wire, wherein at least one of the proximal end of the implant and the distal end of the implant comprise apices and at least one loop of the at least three loops engages at least one apex, and wherein each apex engages a loop of the at least three loops.

13. The deployment system of claim 12, wherein both of the proximal and distal retaining mechanisms comprises at least three loops, each loop engaging an end of the implant and engaging the at least one common release wire.

14. An implant deployment system, comprising:
a deployment device; and
a self-expanding implant disposed on the deployment device and having a proximal end, a distal end, a central portion between the proximal end and the distal end, a first expanded configuration and a second expanded configuration, a stent disposed adjacent one of or both of the proximal and distal ends;
the deployment device comprising:
an implant release mechanism for releasably retaining the implant on the deployment device, the implant release mechanism including an elongate implant support having a proximal implant restraining location disposed substantially adjacent the implant proximal end and a distal implant restraining location disposed substantially adjacent the implant distal end; a proximal wire holding element at the proximal implant restraining location and a distal wire holding element at the distal implant restraining location; and at least one common release wire having an implant proximal end restraining portion and an implant distal end restraining portion, wherein one of or both of the proximal wire holding element and the distal wire holding element comprises at least three loops, wherein each of the at least three loops of the one or both of the proximal wire and distal wire holding elements engages an end of the implant and an implant end restraining portion of the at least one common release wire, and wherein each loop of the plurality of loops forms a loop between an end of the implant and the at least one common release wire;

where in the first expanded configuration the release wire proximal end restraining portion is restrained by the proximal wire holding element and the release wire distal end restraining portion is restrained by the distal wire holding elements so as to restrain the implant at both the proximal and distal locations;

where in the first expanded configuration the at least one release wire restrains both the proximal and distal ends of the implant without restraining the central portion of the implant such that the central portion is at least partially expanded relative to the proximal and distal implant ends, wherein the at least three loops are comprised of a single thread that is coupled by the at least three loops to all of the apices of the stent.

\* \* \* \* \*